(12) United States Patent  (10) Patent No.: US 6,638,065 B2
Fischer et al.  (45) Date of Patent: Oct. 28, 2003

(54) QUAD CUTTER TOOL FOR REMOVING SYRINGE DIVIDER

(75) Inventors: Dan E. Fischer, Sandy, UT (US); Bruce S. McLean, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 9 days.

(21) Appl. No.: 10/024,117

(22) Filed: Dec. 17, 2001

(65) Prior Publication Data

US 2003/0113687 A1 Jun. 19, 2003

(51) Int. Cl.[7] .................................................. A61C 5/04
(52) U.S. Cl. ........................ 433/89; 433/90; 222/581.4
(58) Field of Search ........................... 604/218; 433/83, 433/89, 90; 222/541.2, 541.7, 541.8

(56) References Cited

U.S. PATENT DOCUMENTS

| | | | |
|---|---|---|---|
| 2,515,956 A | 7/1950 | Greenberg | 128/218 |
| 2,537,550 A | 1/1951 | Roos | 128/218 |
| 3,581,399 A | 6/1971 | Dragan | 32/60 |
| 3,724,076 A | 4/1973 | Schmitz | 32/60 |
| 3,884,231 A | 5/1975 | Peters | 128/235 |
| 3,900,954 A | 8/1975 | Dragan | 32/60 |
| 4,189,065 A | 2/1980 | Herold | 222/46 |
| 4,198,756 A | 4/1980 | Dragan | 222/326 |
| 4,295,828 A | 10/1981 | Rudler | 433/90 |
| 4,312,343 A | 1/1982 | La Veen et al. | 128/218 |
| 4,391,590 A | 7/1983 | Dougherty | 433/90 |
| 4,457,712 A | 7/1984 | Dragan | 433/90 |
| 4,472,141 A | 9/1984 | Dragan | 433/90 |
| D277,134 S | 1/1985 | Dragan | D24/24 |
| 4,492,576 A | 1/1985 | Dragan | 433/90 |
| 4,540,405 A | 9/1985 | Miller et al. | 604/232 |
| 4,569,662 A | 2/1986 | Dragan | 433/89 |
| 4,619,613 A | 10/1986 | Dragan | 433/90 |
| 4,643,724 A | 2/1987 | Jobe | 604/232 |
| D289,682 S | 5/1987 | Dragan | D24/16 |
| 4,682,950 A | 7/1987 | Dragan | 433/90 |
| D292,825 S | 11/1987 | Dragan | D24/16 |
| 4,708,650 A | 11/1987 | Holewinski et al. | 433/90 |
| 4,710,179 A | 12/1987 | Haber et al. | 604/211 |
| 4,767,326 A | 8/1988 | Bennet et al. | 433/90 |
| 4,768,954 A | 9/1988 | Dragan | 433/90 |
| 4,784,607 A | 11/1988 | Francois | 433/90 |
| 4,863,072 A | 9/1989 | Perler | 222/390 |
| 4,872,936 A | 10/1989 | Engelbrecht | 156/307.3 |
| 4,915,695 A | 4/1990 | Koobs | 604/191 |
| 4,963,093 A | 10/1990 | Dragan | 433/90 |
| D315,956 S | 4/1991 | Dragan | D24/14 |
| 5,052,927 A | 10/1991 | Discko, Jr. | 433/90 |
| 5,122,057 A | 6/1992 | Discko, Jr. | 433/90 |
| 5,318,544 A | 6/1994 | Drypen et al. | 604/210 |
| 5,387,103 A | 2/1995 | Fischer | 433/89 |
| 5,464,348 A | 11/1995 | Fischer et al. | 433/26 |
| 5,618,273 A | 4/1997 | Fischer | 604/211 |

Primary Examiner—Cary E. O'Connor
(74) Attorney, Agent, or Firm—Workman, Nydegger

(57) ABSTRACT

A syringe system for delivering a dental material comprises a barrel configured for containing the material, a plunger configured for extruding the material, a divider configured for sectionalizing the material while it is being extruded, and a tool configured for detachment of the divider. The divider comprises at least one cutting plate that is affixed to the barrel and the tool comprises at least one recess configured for engaging the at least one cutting plate when the tool is inserted within the barrel, such as in a press fit arrangement. When the tool is axially rotated relative to the barrel, the at least one cutting plate can be effectively sheared away from the barrel. The tool may comprise a cap that is configured for sealably closing the syringe or a tool separate from the syringe.

20 Claims, 8 Drawing Sheets

QUAD CUTTER TOOL FOR REMOVING SYRINGE DIVIDER

BACKGROUND OF THE INVENTION

1. The Field of the Invention

The present invention generally relates to syringe systems used for storing and dispensing pliable materials, and, more specifically, to dental syringe systems capable of providing controllable doses of the pliable materials.

2. The Relevant Technology

In the dental industry, it is common for dental composites and other restoration materials to be stored and dispensed from syringes. Syringes are useful because they are compact and they enable the dental practitioner to generally control the quantity of material that is expelled out of the syringe at any given time. Sometimes, however, the barrel of the syringe is too wide for enabling sufficient control over the expulsion of the composite material out of the syringe. In particular, when the composite material is extruded out of the syringe barrel, it is sometimes difficult for the dental practitioner to partition and remove a desired dosage of the composite from the barrel.

One device that has been developed to overcome the aforementioned problems is a syringe with a divider located at the tip. The divider comprises cutting plates that sectionalize the composite material while it is extruded. The unique divider configuration, known as the QUADRASPENSE®, may comprise various combinations and configurations of cutting plates for controlling the shape and size of the sectionalized material as it is expressed. The cutting plates are also useful for accommodating the removal of the sectionalized material once it is expressed out of the syringe barrel. For example, a spatula or another scrapping tool can be pressed through the sectionalized material and against the cutting plates, thereby enabling the scrapping tool to scrape away and easily remove a desired quantity of material. Syringes having this design are described more fully in U.S. Pat. No. 5,387,103, issued to Fischer, and are presently sold by UTRADENT PRODUCTS, INC. of South Jordan, Utah.

One limitation of syringes with cutting plates, however, is that the cutting plates are securely affixed to the barrels of the syringe, which inhibits the dental practitioner from removing the cutting plates, even when the cutting plates are no longer needed or desired. The cutting plates may not be desired, for instance, when large amounts of composite are required during the dental procedure. The cutting plates are also not desired when most of the composite material is already expelled out of the syringe and the cutting plates obstruct the plunger from expelling the residual portions of the composite material from the barrel.

Accordingly, it is sometimes desirable to remove the cutting plates from the syringe. However, as mentioned above, the cutting plates are typically affixed to the barrel with a secure bond that is created at the time of manufacture, such as during an injection molding process. There is currently no tool that is specifically designed for removing the cutting plates from the QUADRASPENSE® type syringe systems. Therefore the dental practitioner must currently use pliers, a knife, or another device to separate the cutting plates from the barrel of the syringe. It will be appreciated that this is inconvenient, in part, because it can be difficult to find pliers or a knife that is suitably sized for being inserted within the barrel in a manner that is sufficient for cutting or pulling the cutting plates cleanly, away from the sides of the barrel. Furthermore, the use of a cutting device to remove the cutting plates can be risky, inasmuch as the cutting device can slip and cut the dental practitioner.

Accordingly, in view of the foregoing, there is currently a need in the art for improved syringe systems incorporating tools that are configured for facilitating the removal of the cutting plates from the syringe systems and in a manner that does not pose a risk of injury.

SUMMARY OF PRESENTLY PREFERRED EMBODIMENTS

Briefly summarized, presently preferred embodiments of the present invention are directed to improved syringe systems that incorporate dividers and tools that are specifically designed for controllably removing the dividers from the syringe systems when desired.

According to one presently preferred embodiment, the syringe systems of the invention comprise a syringe that is configured for expressing dental material from a syringe barrel incorporating a divider configured for sectionalizing the material as it is expressed from the barrel. The syringe systems also comprise a shearing tool configured for removing the divider from the barrel when it is no longer needed or desired.

The divider comprises at least one cutting plate that is securely affixed to the barrel at the outlet end of the barrel. As the material is expressed out of the barrel it is partitioned by the cutting plate and extruded in sectionalized portions. The divider can be removed when desired by inserting the tool within or next to the outlet end of the barrel and engaging the cutting plate with a shearing force. The shearing tool is configured in size and shape to be inserted within the outlet end of the barrel and to engage the at least one cutting plate. Once the shearing tool is appropriately positioned relative to the barrel so as to engage the cutting plate, as described, the tool is axially rotated relative to the barrel, e.g., about the central axis of the barrel. Axial rotation generates forces that are applied by the shearing tool at the cutting plates, thereby shearing the cutting plates away from the barrel. The shearing tool can be rotated by hand, with the fingers, or with the assistance of another tool, such as pliers. Once the cutting plates have been separated from the barrel then they can easily be removed from the barrel by the shearing tool, which may engage the cutting plates in a press fit arrangement.

According to the invention, the shearing tool may comprise a cap that is configured for sealably closing the syringe during nonuse. The shearing tool may also comprise a that is completely separate from the syringe.

One advantage of the invention is that a dental practitioner can utilize the benefits of syringe incorporating a divider until the divider is no longer desired, such as, for example, when the material within the syringe is almost entirely exhausted and the plunger of the syringe is inhibited by the divider from extruding the residual portions of the material. The invention then enables the practitioner to easily remove the undesired divider when it is no longer needed. The tool may be specifically sized so as to be inserted within the outlet end of the barrel and about the divider. In this way, the divider can be removed cleanly, with minimal effort, and without the risks posed by sharp cutting devices.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof, which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

A detailed description of the syringe system of the invention will now be provided with specific reference to figures illustrating preferred embodiments of the invention. It will be appreciated that like structures will be provided with like reference designations.

To provide assistance in construing the scope of the invention, definitions to terms used throughout the application will now be provided. The term "shear" as used herein generally refers to separating two items that are connected together with a force that is sufficient to break any bonds of affixation between the two items and which generally causes the two items to move in opposite directions with respect to each other without causing a change in the general shape of either item.

The term "pliable material" as used herein generally refers to a material that can be easily deformed or shaped. The term "pliable material" can be construed to include any material that that has a very high degree of viscosity, characterized by a soft clay or paste type consistency, yet is deformable enough to be applied through a syringe. According to one embodiment, the term "pliable material" refers specifically to dental composite materials used for dental applications.

Figure 1:
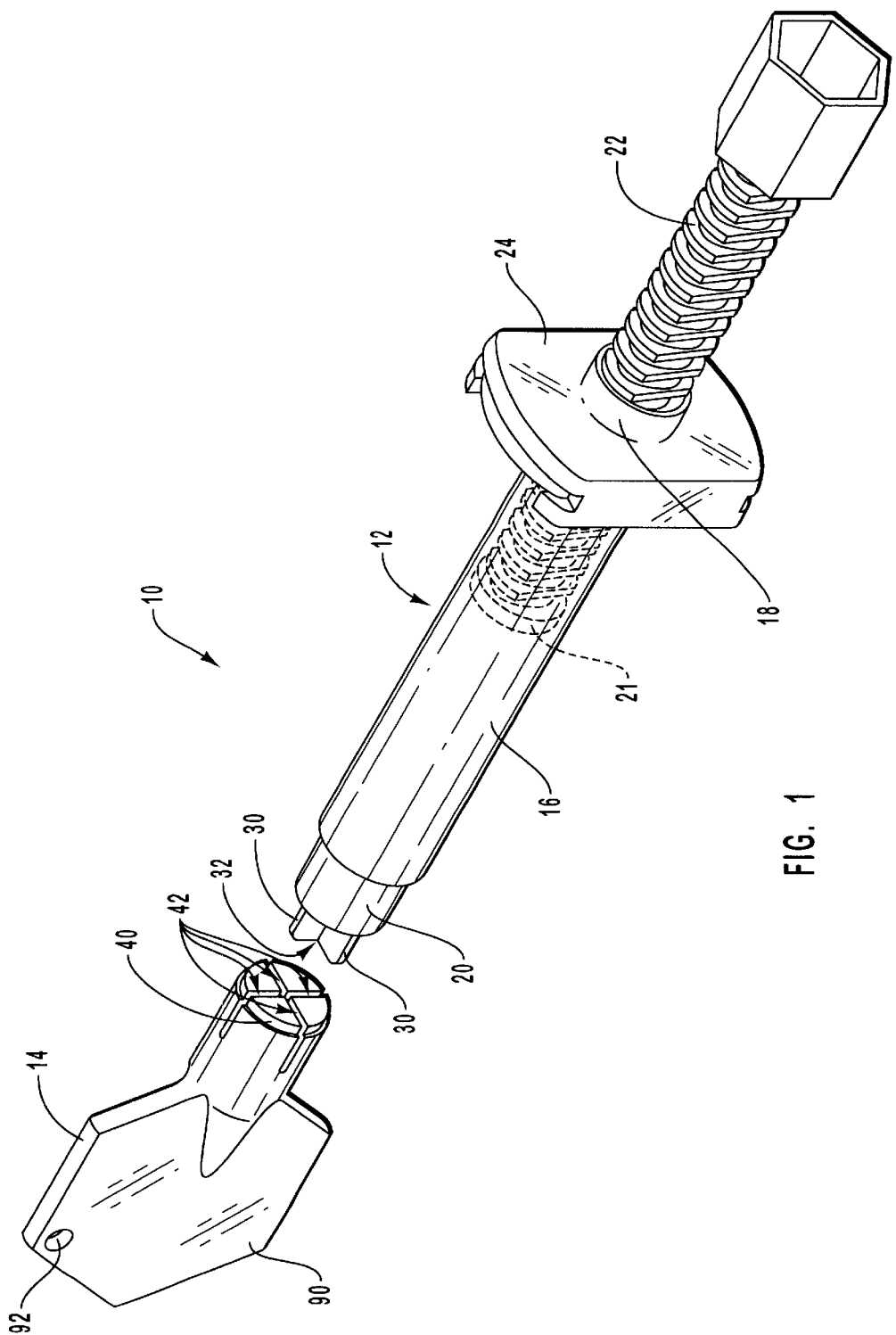
FIG. 1 illustrates a perspective view of one embodiment of the syringe system of the invention that includes a syringe having a divider and a shearing tool configured for shearing the divider from the syringe.

Reference is first made to FIG. 1, which illustrates one exemplary embodiment of the syringe system 10 of the invention. As shown, the syringe system 10 generally includes a syringe 12 configured to express a pliable material during a dental procedure and a shearing tool 14 configured for removing a divider that is attached to the syringe 12. The syringe 12 and the shearing tool 14 are each described below.

The syringe 12 includes a barrel 16 extending from an inlet end 18 to an outlet end 20. The barrel 16 is specifically configured to hold a pliable material, such as a dental composite material (not shown). The dental composite material is contained within the barrel 16 and is expelled from the outlet end 20 of the barrel 16 when a head 21 of a plunger 22 is advanced through the barrel 16 from the inlet end 18 to the outlet end 20.

According to one embodiment, the plunger 22 is threaded and engages a threaded coupling 24 connected with the inlet end 18 of the barrel 16. As the plunger 22 is rotated in a clockwise direction, the plunger 22 is advanced by the threaded coupling 24 through the barrel 16 towards the outlet end 20 of the barrel 16. When the plunger 22 is rotated in a counterclockwise direction, the plunger 22 is forced by the threaded coupling 24 to retract towards the inlet end 18 of the barrel 16. According to another embodiment, the plunger 22 is forced back and forth within the barrel 16 as the plunger 22 is rotated in directions opposite from those mentioned above. According to yet another embodiment, the plunger 22 does not include a threaded coupling 24, rather the plunger 22 is forced through the barrel 16 simply by applying an appropriate force to the back of the plunger 22.

As mentioned above, pliable material within the barrel 16 is pressed towards and through the outlet end 20 of the barrel 16 by the force of the plunger 22. As the pliable material is pressed through the outlet end 20 of the barrel 16 it is sectionalized by cutting plates 30 of a divider 32 that is attached at the outlet end 20 of the barrel 16. The divider 32 may include any number of cutting plates 30 configured to sectionalize the material into any number of desired sections having any desired proportions. According to one embodiment, the divider 32 includes four cutting plates 30 configured for dividing the material into four equally proportioned sections. The four cutting plates may be considered to be two bisecting cutting plates. This embodiment is illustrated in FIGS. 1–7. According to another embodiment, the divider may consist of only a single cutting plate configured to divide the material into two equally proportioned sections when it is expelled out of the barrel 16.

The dividers 32 are generally useful for facilitating removal of the material from the syringe 12. In particular, the dividers 32 can be utilized as a scraping surface against which a scraping tool can bias while scraping away portions of the pliable material from the syringe 12. Dividers and scraping tools, which are used to facilitate the removal of a material from a syringe, are well known by those skilled in the art.

Although dividers are generally useful for their intended purpose, they are sometimes undesirable. In particular, once the plunger 22 is completely inserted within the barrel 16 so that it is biased against the divider 32 it can no longer expel material out of the syringe. The divider 32 effectively prevents the plunger 22 from pushing the residual portions of the material out of the syringe. Accordingly, in order to remove the residual portions of the material from the syringe 12, it may be necessary to scrape around the internal circumference of the barrel 16 and between the cutting plates 30 of the divider 32 with a scraping tool. This, however, can be difficult because the divider 32 hinders scraping tools from being manipulated inside of the barrel 16. Accordingly, it will be appreciated that it can sometimes be useful to remove the divider 32 from the barrel 16 so that the plunger 22 can push the remaining portions of the material out of the barrel 16.

One method for removing the divider 32 from the barrel 16 is to use a pulling device, such as a pair of pliers to grab and pull the divider 32 away from the barrel 16. This method, however, has proven to be awkward and inadequate. The bond between the divider 32 and the barrel 16 is strong enough that it is often necessary to apply a great amount of force to the divider 32 before it can be detached. However, because pliers are not specifically designed to be inserted within a small barrel 16, while at the same time being opened to grab the divider 32, they can often only be used to grab a hold of small portions of the divider 32 that protrude out of the barrel 16. Accordingly, pliers, as well as other tools, are prone to slip off of the divider 32 while detaching the divider 32 from the barrel 16. Furthermore, even when the pliers do not slip off of the divider 32, they generally cause the forces applied to the divider 32 be distributed unevenly which can cause the divider 32 to be stretched and torn or ripped abnormally away from the barrel, with small portions of the divider 32 remaining attached to the barrel 16. The stretching and tearing of the divider is largely a function of not being able to apply the forces directly at the locations where the divider 32 is attached to the barrel 16.

Another method for removing the divider 32 is to use a cutting device, such as a knife to cut the divider 32 from the barrel 16. Cutting devices, however, create an unnecessary element of risk to the person removing the divider 32. Furthermore, because cutting devices are not typically configured in size and shape for being inserted within a small syringe barrel 16, they also are generally unable to cleanly separate the divider 32 from the barrel 16. It will be appreciated that any portions of the divider 32 that are not entirely removed from the barrel 16 can obstruct passage of the plunger 22 through the barrel 16, effectively preventing the plunger 22 from expelling the remaining portions of the material.

The present invention overcomes the problems mentioned above by providing a shearing tool 14 that is specifically configured in size and shape to be inserted within or next to the barrel 16 of the syringe 12 and to apply a shearing force directly at the locations where the divider 32 is connected to the barrel 16. According to one embodiment, the shearing tool 14 is comprised of plastic. Plastic is a good material because it is relatively inexpensive. It will be appreciated, however, that other materials can also be used, such as for example ceramics and metals. Ceramics and metals are also good materials because they are relatively rigid which can be useful when shearing the divider 32 from the barrel 16.

Figure 2:
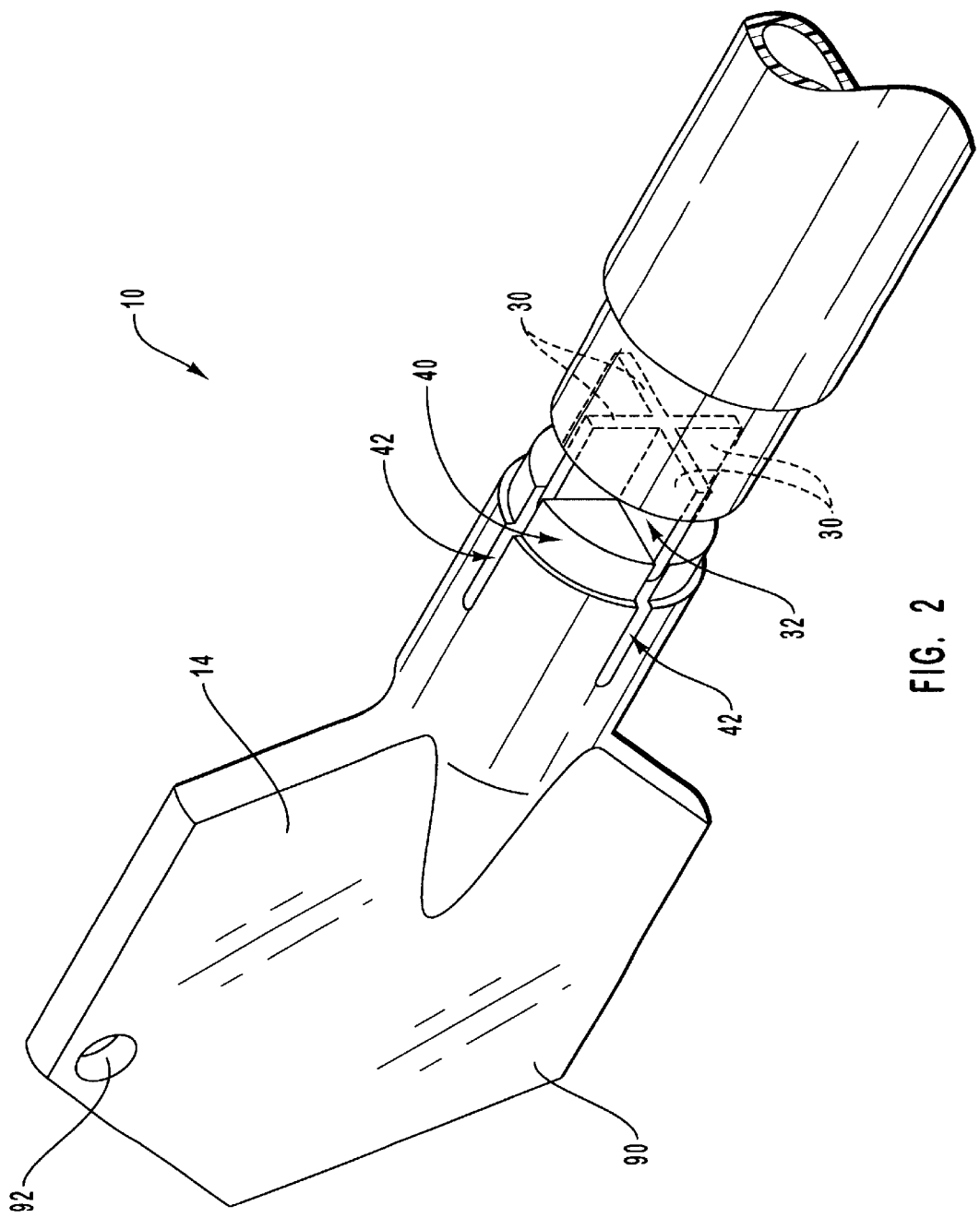
FIG. 2 illustrates a perspective view of the syringe system shown in FIG. 1, in which the shearing tool is positioned in an initial engagement position with the divider.

Turning now to FIG. 2, phantom imaging is used to show how the divider 32 is attached to the inside of the barrel 16. According to one embodiment, the divider 32 is molded together with the barrel 16 at the time of manufacture. The divider 32 can also be attached to the barrel 16 by any other suitable means, including, but not limited to, press fitting, adhesive bonding, and the like. In order to cleanly break the bond between the divider 32 and the barrel 16 it is desirable to apply a shearing force at the locations where the divider 32 is attached to the barrel 16. This is possible, according to the present invention by using a shearing tool 14 that is configured in size and shape to engage the cutting plates 30 of the divider 32 at the locations adjacent to where the cutting plates 30 are affixed or otherwise connected with the barrel 10.

As shown in FIG. 2, the shearing tool 14 of the invention comprises a stem 40 that is configured into the general shape of the barrel 16 and includes recesses 42 that are configured to receive and engage the cutting plates 30 of the divider 32 when the stem 40 is inserted within the outlet end 20 of the barrel 16. It will be appreciated that as the stem is inserted within barrel 16 that the stem 40 will push any material back into the barrel 16. To avoid any undesired compressive forces, the plunger can be retracted prior to inserting the stem 40 into the barrel 16.

Figure 3:
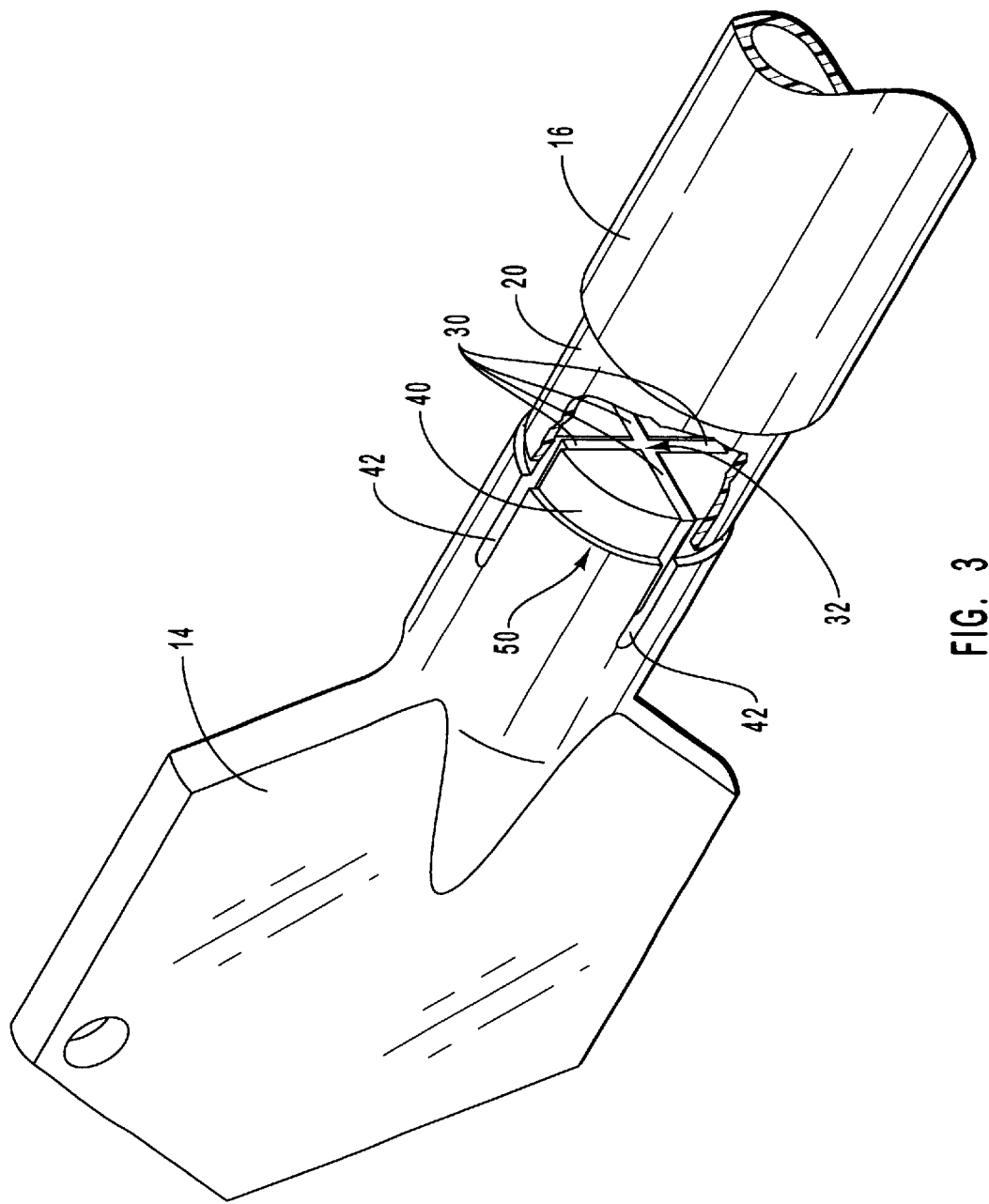
FIG. 3 illustrates a perspective view of the syringe system shown in FIG. 2, in which the divider is completely engaged within recesses formed in the shearing tool.

FIG. 3 illustrates a partial cross-sectional view of the syringe system 10 of the invention in which the shearing tool 14 has been inserted into the barrel 16 and in which the cutting plates 30 of the divider 32 have been fully received within the recesses 42 of the shearing tool 14. As shown, the shearing tool 14 may also include a lip 50 for gauging how far the stem is to be inserted within the barrel 16. The lip 50 can be useful, for example, for ensuring that the cutting plates 32 are entirely engaged within the recesses 42 of the shearing tool 14. In this way, the shearing forces can be applied evenly along the cutting plates 30 so as to facilitate shearing the cutting plates 32 cleanly away from the barrel 16. It will be appreciated that according to certain embodiments the stem 40 of the shearing tool 14 may be inserted beyond the cutting plates 30.

Figure 4:
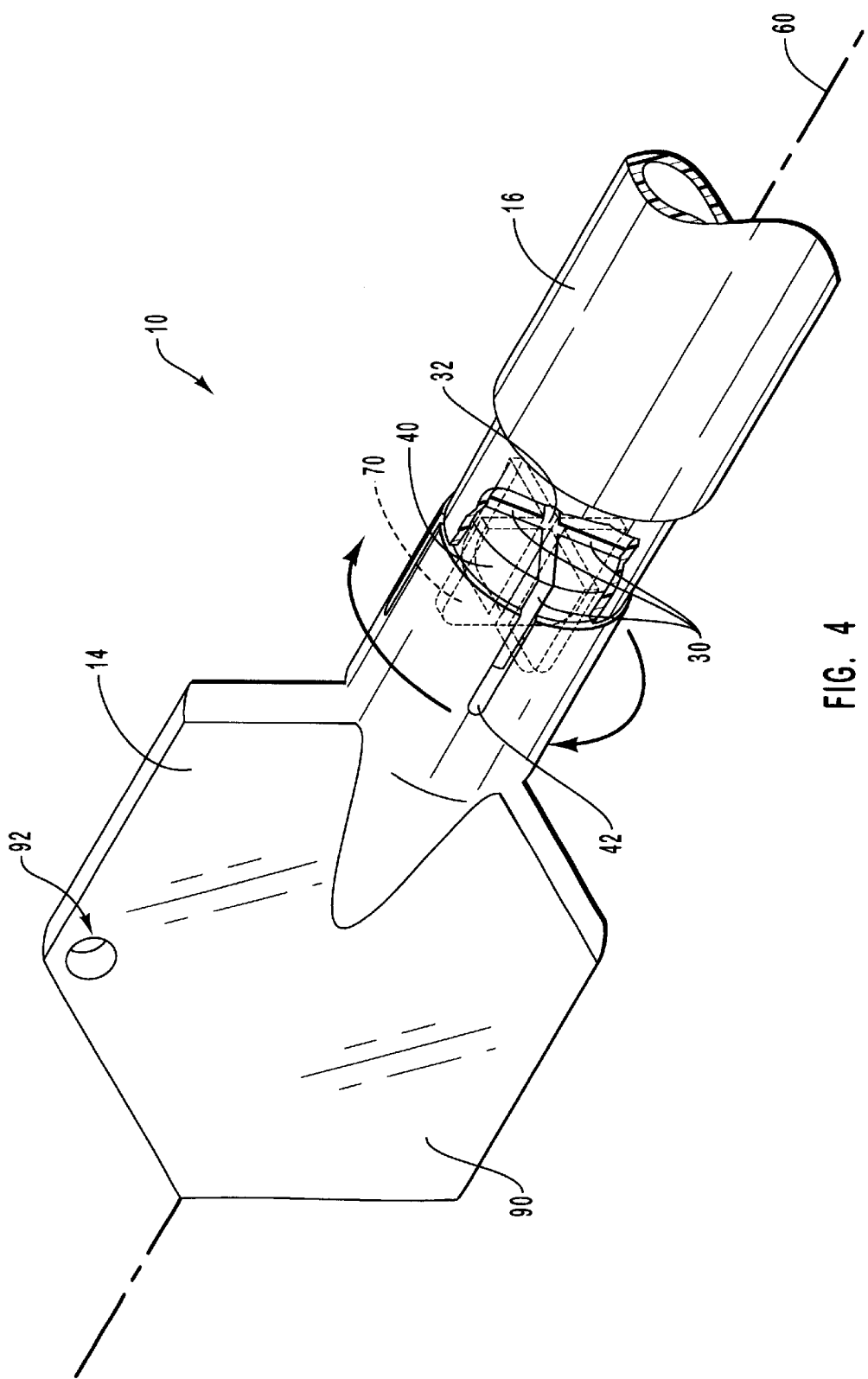
FIG. 4 illustrates a perspective view of the syringe system shown in FIG. 3, in which the shearing tool is rotated and the divider is sheared away from the barrel of the syringe.

Turning now to FIG. 4, it is shown how the shearing tool 14 can be used to shear the divider 32 away from the barrel 16. As shown, the divider 32 is shorn away from the barrel 16 when the shearing tool 14 is axially rotated about the central axis 60 of the barrel 16 within or next to the outlet end 20 of the barrel 16. A phantom image 70 is provided to illustrate the previous location of the divider 32 before the shearing tool 14 was rotated. It will be appreciated that the divider 32 can be separated from the barrel 16 by rotating the shearing tool 14 in either a clockwise or a counterclockwise direction with respect to the barrel 16.

According to one embodiment the stem 40 of the shearing tool 14 is configured in size and shape to fit within the barrel 16 so that the stem 40 engages the internal surfaces of the barrel 14. This enables the shearing tool to apply shearing forces along the entire length of the cutting plates 30 where they engage the barrel 16, so as to cleanly shear the cutting plates 30 away from the barrel 16. It will be appreciated that this is an improvement over the prior art.

According to other embodiments the stem 40 of the shearing tool 14 is sized smaller than the barrel 16 so that the stem 40 does not engage the interior surfaces of the barrel 16. According to these embodiments, the stem 40 applies shearing forces to the cutting plates adjacent to the locations where the cutting plates 30 are affixed to the barrel 16. It will be appreciated that this is also an improvement over the prior art because the stem 40 of the shearing tool is still able to apply forces uniformly along the entire length of the cutting plates 30, thereby minimizing the likelihood that the divider will stretch and tear abnormally away from the barrel.

Figure 5:
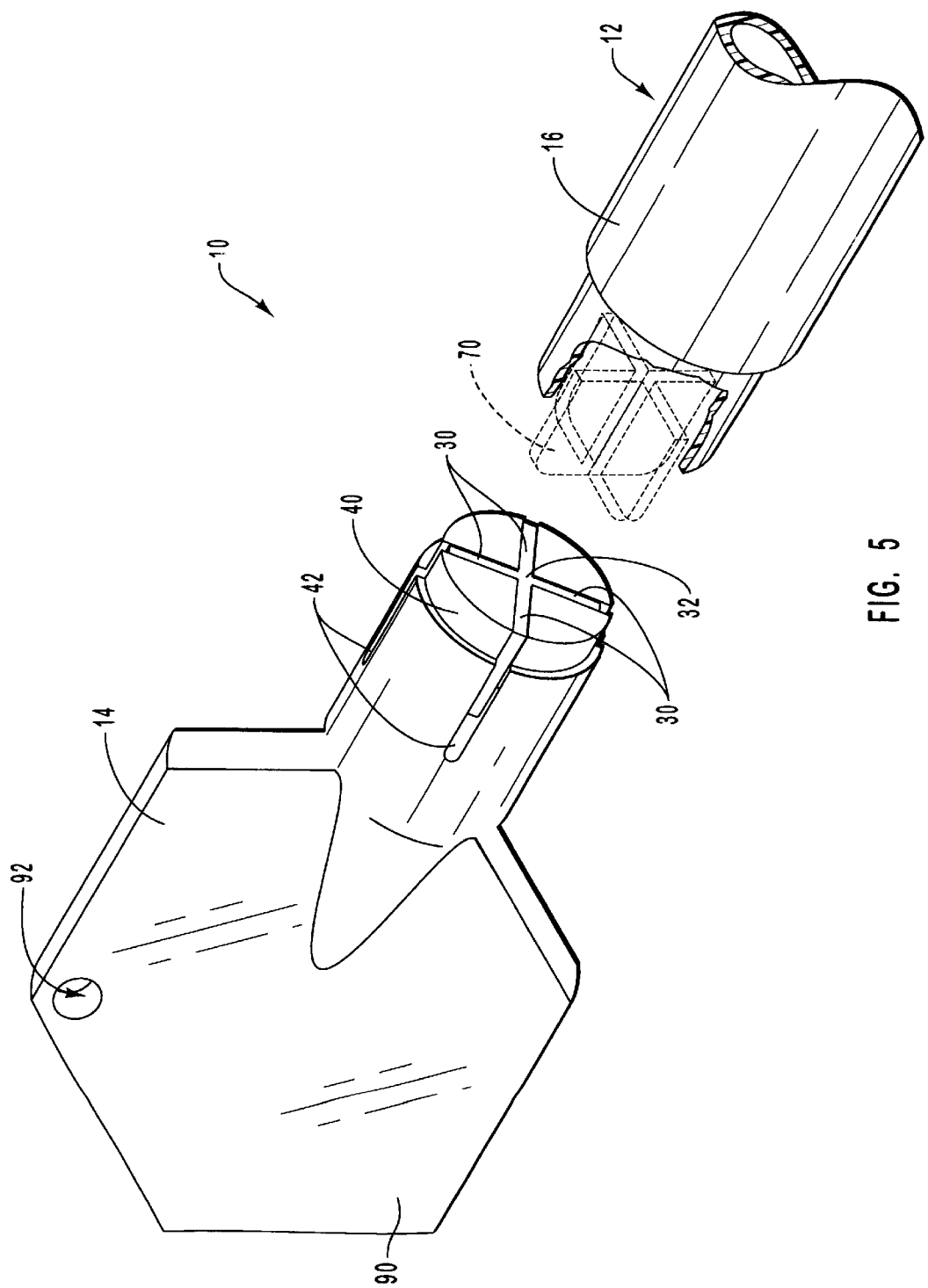
FIG. 5 illustrates a perspective view of the syringe system shown in FIG. 4, in which the shearing tool and the divider have been removed from the barrel.

Once the bond between the divider 32 and the barrel 16 is broken, the shearing tool 14 and the divider 32 can be removed from the barrel 16. This may occur in two steps or in a single step. In particular, the shearing tool 14 can first be removed and then the divider 32 can be removed, or alternatively, the divider 32 can be removed simultaneously with the shearing tool 14. According to one embodiment, as shown in FIG. 5, the divider 32 engages the recesses 42 of the shearing tool 14 in a press fit arrangement so that when the shearing tool 14 is removed from the barrel 16 the divider 32 is pulled out from the barrel 16 by the shearing tool 14. This embodiment is also useful for ensuring that the material within the syringe 12 is cleanly scraped off of the cutting plates 30 and into the barrel 16 when the shearing tool 14 is first inserted into the barrel 16.

Figure 6:
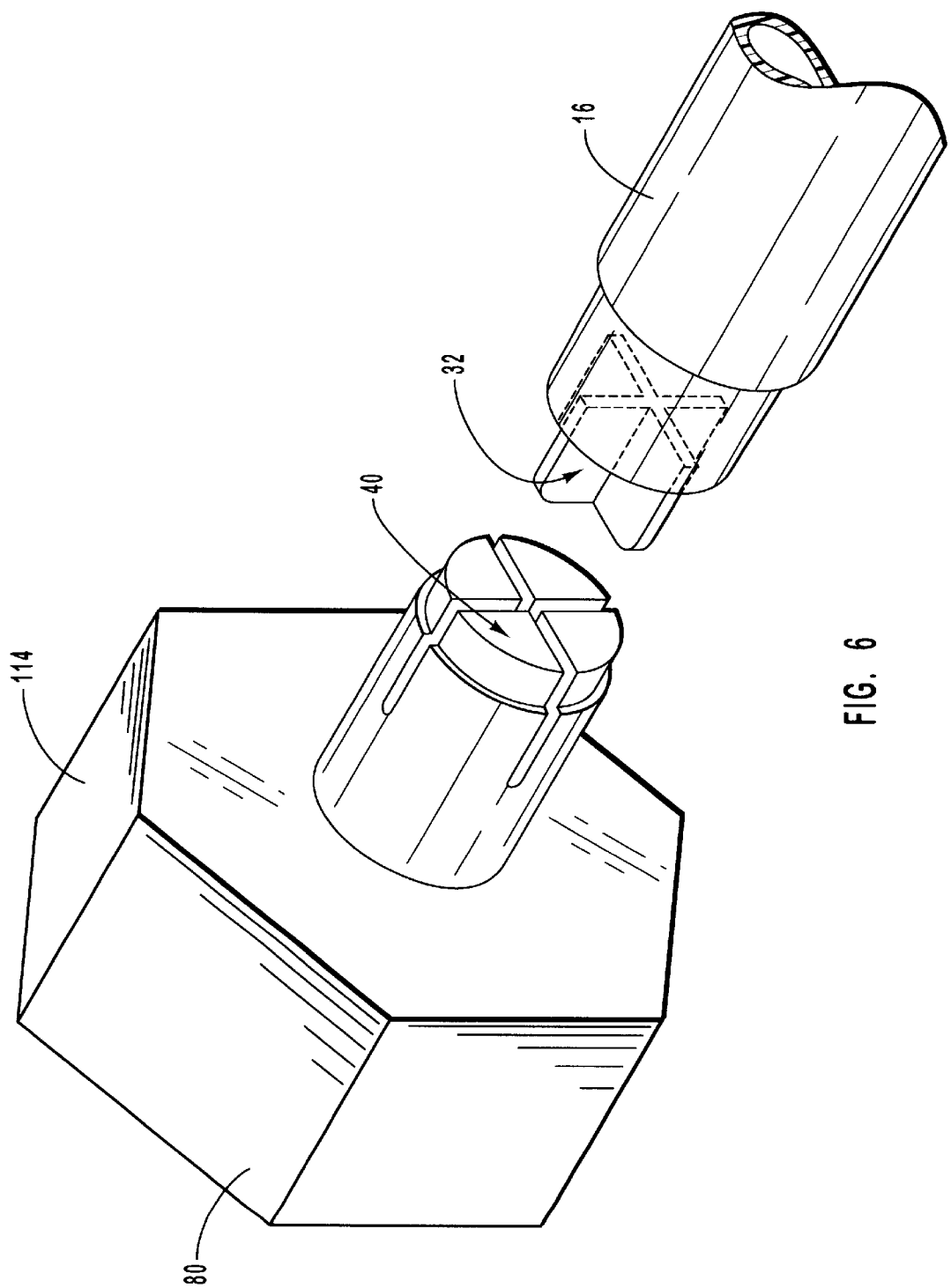
FIG. 6 illustrates a perspective view of one embodiment of the syringe system of the invention that includes a syringe having a divider and a hexagonally shaped head.

FIG. 6 illustrates one embodiment of the invention in which the head 80 of the shearing tool 114 is configured in the shape of hexagon. This embodiment is useful for enabling a wrench or other tool to grip the head 80 to facilitate the rotation of the shearing tool 14 within the barrel 16. The flattened shape of the head 90 in FIGS. 1–5 is useful when using fingers to rotate the shearing tool 14. To facilitate gripping of the head 90, the head 90 may be textured. As shown in FIGS. 1–5, the head of the shearing tool 14 may also include a hole 92 configured for connecting the shearing tool onto a chain so that the shearing tool is not easily misplaced.

Figure 7:
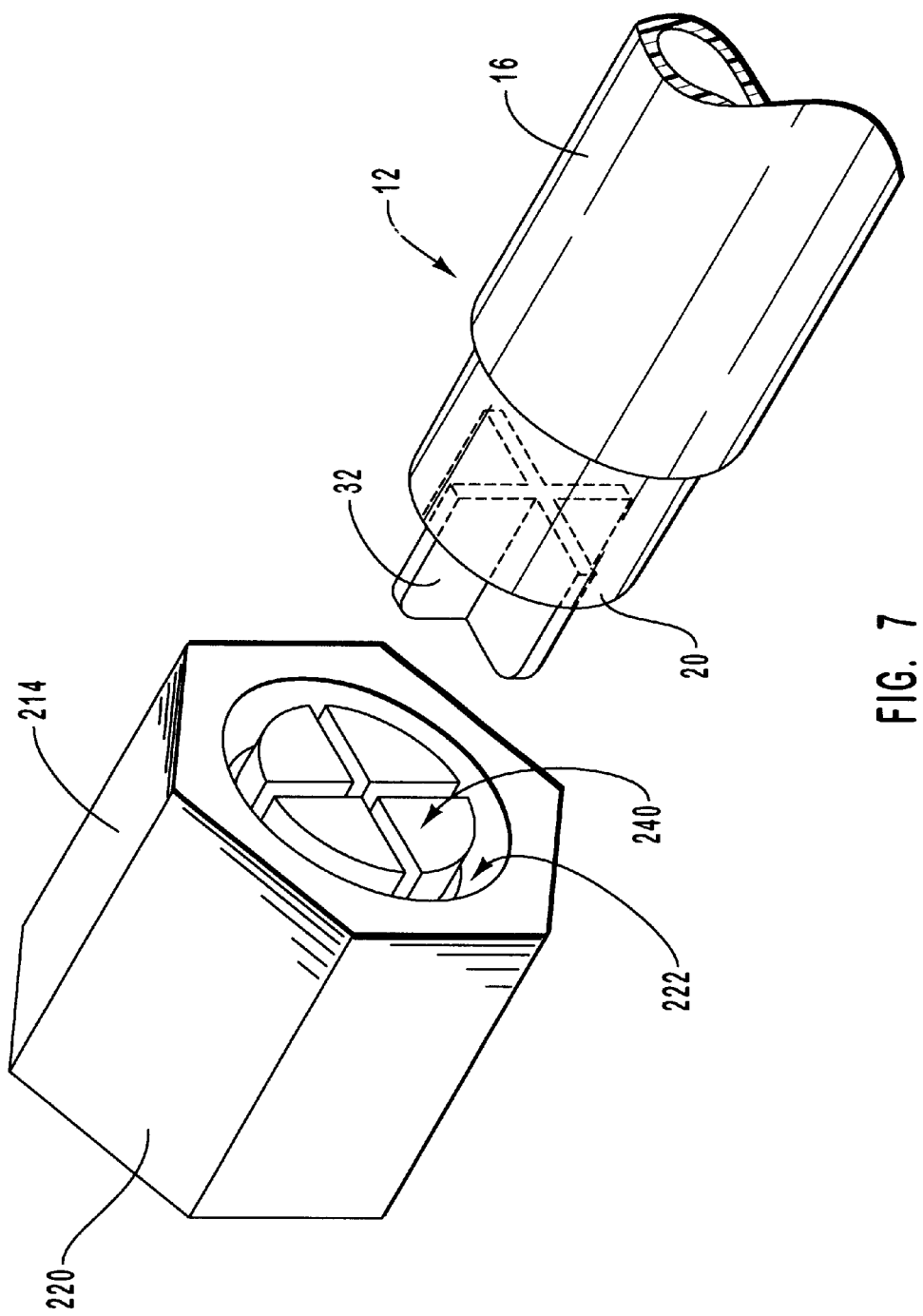
FIG. 7 illustrates a perspective view of one embodiment of the syringe system of invention that includes a syringe having a divider and a cap for the syringe that is configured for shearing the divider from the syringe.

According to another embodiment, as shown in FIG. 7, the shearing tool 214 may also comprise the cap 220 to the syringe 12. This embodiment is particularly useful for ensuring that the shearing tool 214 is not misplaced or lost during nonuse. As shown, the cap 220 is configured with a cylindrical recess 222 configured to receive the outlet end 20 of the barrel 16. When the cap 220 engages the outlet end 20 of the barrel 16, the barrel 16 is sealed closed so that any material within the barrel 16 can be preserved during periods of nonuse. The cap 220 can also operate as a shearing tool 214 to separate and remove the divider 32 from the barrel 16 when the divider 32 is no longer needed or desired. In particular, the cap 220 further includes a stem 240 configured to engage the divider 32. The cap 220 can remove the divider 32 from the barrel 16 by rotating the cap 220 with the stem 240 of the cap 220 inserted within the outlet end 20 of the barrel 16, as generally described above.

Figure 8:
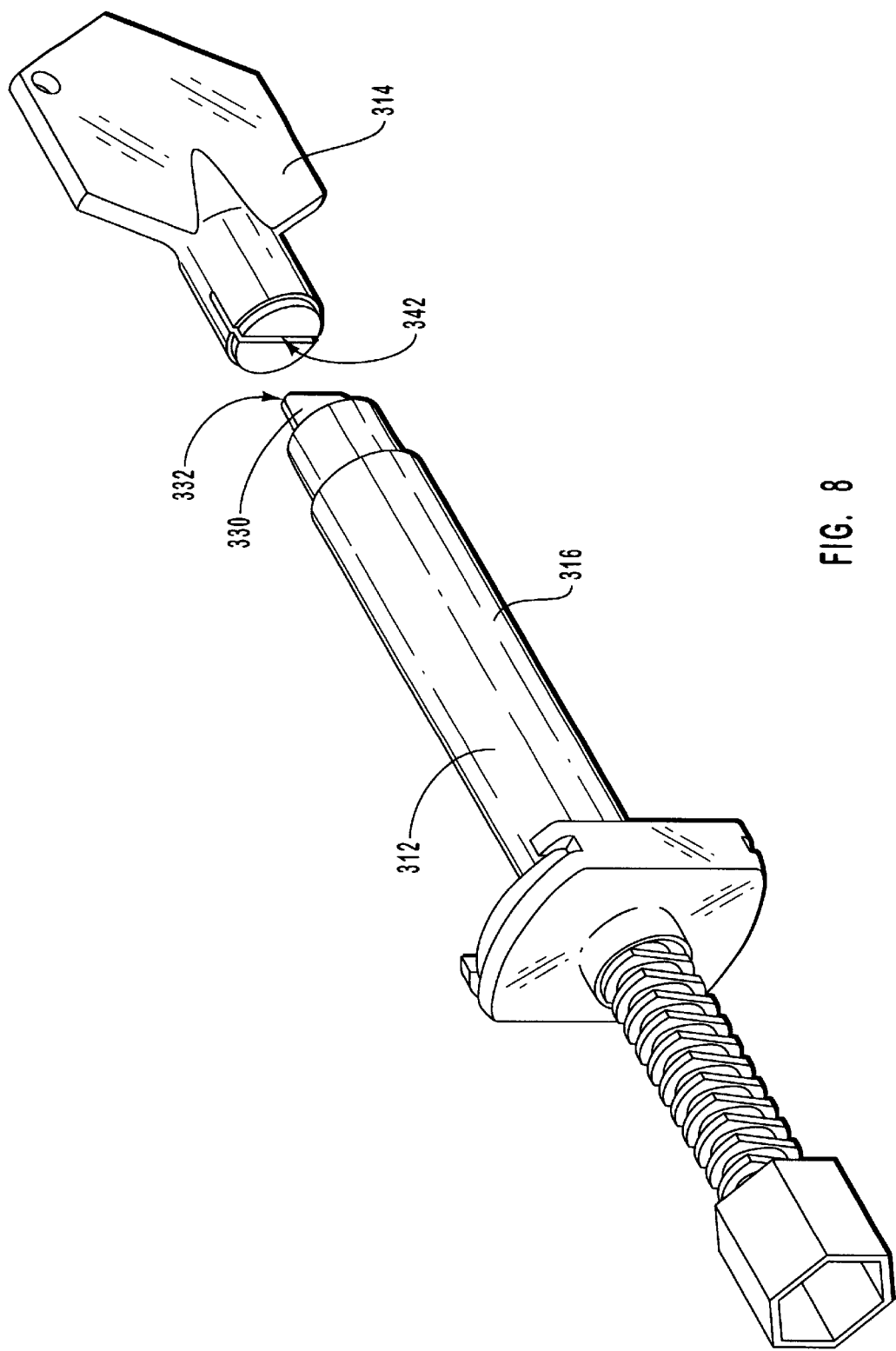
FIG. 8 illustrates a perspective view of one embodiment of the syringe system of the invention that includes a syringe having a divider composed of a single cutting plate and a shearing tool configured for shearing the divider from the syringe.

FIG. 8 illustrates one alternative embodiment of the invention in which the syringe 312 includes a divider 332 attached to the inside of barrel 316 and having only a single cutting plate 330 and in which the shearing tool 314 includes a corresponding recess 342 configured to engage the cutting plate 330. It will be appreciated, however, that the shearing tool 314 may include any number of recesses configured for engaging any number of cutting plates and will still be operational to engage and remove the cutting plate 330 shown.

In summary, the syringe systems of the invention generally include a syringe having a divider and a tool configured for removing the divider from the syringe. The syringe systems of the invention are an improvement over the prior art for at least providing a means for effectively removing the divider from the syringe.

It will be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A syringe system configured for expressing a pliable material, the syringe system comprising:
    a barrel configured for containing a pliable material, the barrel comprising an inlet end and an outlet end;
    a plunger configured for pushing the pliable material contained in the barrel to the outlet end of the barrel;
    a divider configured for sectionalizing portions of the pliable material when it is pushed through the outlet end of the barrel, wherein the divider comprises at least one cutting plate that is affixed within the outlet end of the barrel; and
    a tool configured that comprises at least one recess that is sized and shaped so as to engage the at least one cutting plate and detach the cutting plate from the barrel when the tool is axially rotated relative to the barrel.

2. A syringe system as recited in claim 1, wherein the tool comprises a head and a stem, wherein the stem is configured in size and shape so as to engage the at least one cutting plate in a press fit arrangement.

3. A syringe system as recited in claim 2, wherein the head is textured.

4. A syringe system as recited in claim 2, wherein the head comprises surfaces configured for receivably engaging at least one of pliers and another device capable of rotating the tool relative to the barrel.

5. A syringe system as recited in claim 4, wherein the head comprises a hexagonal shape.

6. A syringe system as recited in claim 4, wherein the tool comprises a cap configured for sealably closing the outlet end of the barrel.

7. A syringe system as recited in claim 2, wherein the stem of the tool is configured so as to be inserted into the outlet end of the barrel a distance so that the at least one cutting plate is entirely received within the at least one recess.

8. A syringe system as recited in claim 1, wherein the tool is configured so as to be inserted into the outlet end of the barrel in order to engage the at least one cutting plate within the barrel.

9. A syringe system as recited in claim 1, wherein the divider includes a plurality of cutting plates and the tool includes a plurality of recesses configured for engaging the plurality of cutting plates in a press fit arrangement.

10. A syringe system as recited in claim 1, wherein the tool comprises a substantially rigid material.

11. A syringe system as recited in claim 10, wherein the tool comprises at least one plastic.

12. A syringe system as recited in claim 1, wherein the plunger is threaded and includes a head that slides within the barrel when the plunger is rotated within a threaded coupling attached to the inlet end of the barrel.

13. A syringe configured for delivering a pliable material, the syringe comprising:
    a barrel configured for containing a pliable material, the barrel comprising an inlet end and an outlet end;
    a plunger configured for moving through the barrel and for pushing the pliable material contained in the barrel to and through the outlet end of the barrel;
    a divider configured for sectionalizing portions of the pliable material when it is pushed to and through the outlet end of the barrel, wherein the divider comprises at least one cutting plate that is affixed to the barrel within the outlet end; and
    a cap comprising:
        a capping surface sized so as to at least partially enclose an exterior surface of the outlet end of the barrel; and
        a stem sized and shaped so as to be insertable within at least a portion of the outlet end of the barrel, wherein the stem includes at least one recess configured so as to engage the at least one cutting plate within the barrel in a press fit arrangement, and wherein the stem is configured so as to detach the at least one cutting plate from within the barrel when the stem is axially rotated within the barrel.

14. A syringe as recited in claim 13, wherein the stem of the cap is configured so as to be inserted into the outlet end of the barrel in order to engage the entire cutting plate.

15. A syringe system as recited in claim 13, wherein the divider comprises a plurality of cutting plates and the cap comprises a plurality of corresponding recesses.

16. A syringe system as recited in claim 13, wherein the stem is configured so as to engage the at least one cutting plate adjacent to where the cutting plate is affixed to the barrel.

17. A method for removing a divider from a syringe, wherein the divider is affixed to an outlet end of the syringe and is configured for sectionalizing portions of a pliable material contained within the syringe when the material is pushed through the divider, the method comprising:

provide a tool includes at least one recess configured so as to engage at least a portion of the divider with the tool so that at least a portion of the divider is received within the at least one recess; and rotating the tool relative to the syringe so as to detach the divider from the outlet end of the syringe.

18. A method as recited in claim 17, wherein the act of engaging the divider includes inserting a portion of the tool into the outlet end of the syringe.

19. A method as recited in claim 17, wherein the tool comprises a head and a stem, wherein the stem is configured so as to be at least partially inserted into the outlet end of the barrel and engage the divider adjacent to where the divider is affixed to the outlet end of the syringe.

20. A method as recited in claim 19, wherein the stem of the tool is configured so as to be inserted into the outlet end of the barrel so that the entire divider is received within the at least one recess of the tool.

* * * * *

UNITED STATES PATENT AND TRADEMARK OFFICE
CERTIFICATE OF CORRECTION

PATENT NO. : 6,638,065 B2 Page 1 of 1
DATED : October 28, 2003
INVENTOR(S) : Fischer et al.

It is certified that error appears in the above-identified patent and that said Letters Patent is hereby corrected as shown below:

Column 1,
Line 66, please delete "," after "cleanly"

Column 2,
Line 45, after "comprise a" please insert -- device --

Column 3,
Line 31, after "system of" please insert -- the --
Line 60, after "material" please delete the first instance of "that"

Column 5,
Line 20, after "divider 32" please insert -- to --

Signed and Sealed this

Twenty-fourth Day of August, 2004

JON W. DUDAS
*Director of the United States Patent and Trademark Office*